US012678195B2

(12) United States Patent
He et al.

(10) Patent No.: US 12,678,195 B2
(45) Date of Patent: Jul. 14, 2026

(54) RESPIRATORY OBSTRUCTION REMOVAL DEVICE

(71) Applicant: DCSTAR INC., New York, NY (US)

(72) Inventors: Ligui He, New York, NY (US); David Luo, New York, NY (US)

(73) Assignee: DCSTAR INC., New York, NY (US)

( * ) Notice: Subject to any disclaimer, the term of this patent is extended or adjusted under 35 U.S.C. 154(b) by 0 days.

(21) Appl. No.: 19/299,065

(22) Filed: Aug. 13, 2025

(65) Prior Publication Data

US 2025/0366888 A1     Dec. 4, 2025

Related U.S. Application Data

(63) Continuation of application No. 19/036,935, filed on Jan. 24, 2025, which is a continuation of application
(Continued)

(51) Int. Cl.
*A61M 16/06*          (2006.01)
*A61B 17/00*          (2006.01)
(Continued)

(52) U.S. Cl.
CPC ............. *A61B 17/50* (2013.01); *A61M 1/962* (2021.05); *A61M 16/06* (2013.01);
(Continued)

(58) Field of Classification Search
CPC ... A61B 17/50; A61B 17/24; A61B 2017/306; A61B 2217/005; A61B 2017/00561;
(Continued)

(56) References Cited

U.S. PATENT DOCUMENTS 2,428,451 A    10/1947  Emerson
2,737,177 A     3/1956  Anklin
(Continued)

FOREIGN PATENT DOCUMENTS

CN        112932633      6/2021
CN        116059599      5/2023

OTHER PUBLICATIONS

Chang-yi Wang and Deng-chuan Cai; "Hand tool handle design based on hand measurements"; 2017, MATEC Web of Conferences.

*Primary Examiner* — Brandy S Lee
*Assistant Examiner* — Tina Zhang
(74) *Attorney, Agent, or Firm* — HSML P.C.

(57)                    ABSTRACT

A respiratory obstruction removal device, which includes a face mask and a negative pressure generating device. The negative pressure generating device includes a grip section, an extendable tubular body, and an annular interface, connected in sequence. The extendable tubular body has a variable volume cavity. The face mask includes an upper part that fits with the annular interface, a lower part that corresponds to a face of a patient, and a connecting body that links the upper and lower parts. The respiratory obstruction removal device also includes a first one-way valve located on the annular interface and a second one-way valve for unidirectional expulsion of gas to the outside. The grip portion and the extendable tubular body are detachably connected. This design is efficient and easy to carry and transport, suitable for emergency use in different scenarios.

17 Claims, 13 Drawing Sheets

Related U.S. Application Data

No. 18/509,912, filed on Nov. 15, 2023, now Pat. No. 12,239,343.

(51) Int. Cl.
| | |
|---|---|
| *A61B 17/50* | (2006.01) |
| *A61M 1/00* | (2006.01) |
| *A61M 16/20* | (2006.01) |

(52) U.S. Cl.
CPC . *A61M 16/208* (2013.01); *A61B 2017/00561* (2013.01); *A61M 2210/1032* (2013.01)

(58) Field of Classification Search
CPC ....... A61B 2017/308; A61B 2017/242; A61M 16/0075; A61M 1/67; A61M 16/06; A61M 16/0084; A61M 16/208
USPC ............ 128/205.13, 205.24, 205.14, 205.16, 128/204.18, 205.18, 205.19
See application file for complete search history.

(56) References Cited

U.S. PATENT DOCUMENTS

| | | | |
|---|---|---|---|
| 4,934,360 | A | 6/1990 | Heilbron et al. |
| 4,971,053 | A | 11/1990 | Tarrats |
| 5,217,006 | A * | 6/1993 | McCulloch ....... A61M 16/0084 |
| | | | 128/205.24 |
| 5,313,938 | A * | 5/1994 | Garfield ................ A61M 1/684 |
| | | | 128/205.24 |
| 5,628,305 | A | 5/1997 | Melker |
| 5,749,358 | A | 5/1998 | Good et al. |
| 10,052,115 | B2 | 8/2018 | Lih |
| 11,478,575 | B1 | 10/2022 | He |
| 2009/0065729 | A1 | 3/2009 | Worboys |
| 2011/0174309 | A1 | 7/2011 | Anderson |
| 2015/0190158 | A1 | 7/2015 | Lih |
| 2020/0306420 | A1 | 10/2020 | Carver |

* cited by examiner

A

B

C

RESPIRATORY OBSTRUCTION REMOVAL DEVICE

CROSS REFERENCE

This application is a continuation application of U.S. application Ser. No. 19/036,935, filed on Jan. 24, 2025, which is a continuation application of U.S. application Ser. No. 18/509,912, filed on Nov. 15, 2023, and granted as U.S. Pat. No. 12,239,343, the disclosures of which are incorporated by reference.

TECHNICAL FIELD

This disclosure pertains to the field of medical device technology, specifically involving an airway obstruction removal device.

BACKGROUND

Various reasons can lead to the occurrence of obstructions in the airway, resulting in asphyxiation. If emergency aid is not administered within 4-6 minutes, a series of severe consequences may ensue. The lack of oxygen can rapidly progress to unconsciousness, and even cardiac arrest, leading to death in extreme cases. Oxygen is a key element for the normal functioning of the brain. An oxygen deficiency can lead to inadequate blood supply to the brain, resulting in the death of nerve cells and a state of cerebral ischemia. This could further lead to permanent brain damage. Even if the asphyxiated individual survives after timely rescue, cognitive function impairment, motor dysfunction, and other neurological problems may still occur. Moreover, these issues could last a lifetime, severely affecting the quality of life. Additionally, the impact of hypoxia and asphyxiation on heart function cannot be overlooked. Oxygen deficiency may directly affect the heart, causing arrhythmia, myocardial injury, and other heart problems. These issues can further worsen the health condition of the asphyxiated individual and increase the risk of complications. This is particularly the case for populations with already weakened heart function, such as the elderly and chronic disease patients. An asphyxiation event could put added strain on their already fragile hearts, potentially leading to heart attacks or cardiac arrest.

Asphyxiation events can occur at any place and time, including in isolated environments, densely populated areas, or on transportation vehicles. In these situations, due to the lack of effective airway obstruction removal devices or emergency measures, timely emergency assistance may not be provided, thereby further increasing the risk for the individual experiencing asphyxiation. For instance, in outdoor activities, sporting events, swimming, or choking on food, asphyxiation incidents often occur due to the lack of emergency equipment or the inability to immediately transport the individual to a hospital. Even at home, asphyxiation events may happen if there are no timely airway obstruction removal devices or emergency measures available.

Currently, the "Heimlich maneuver" is commonly used for emergency aid for patients with airway obstructions. However, the Heimlich maneuver requires the rescuer to apply sufficient force in the correct position; otherwise, it may result in ineffective relief or injury to the patient. Moreover, there are certain risks and potential complications, such as fractured sternum, internal injuries, or pain, especially if the procedure is performed incorrectly. Therefore, the Heimlich maneuver is not suitable for all causes of asphyxiation. For patients with certain diseases, skeletal structural abnormalities, or other special circumstances, alternative emergency measures may be needed. Given the critical importance of timely airway obstruction removal for the life and health of an individual experiencing asphyxiation, there is a need for an efficient, portable, and easy-to-operate tool for emergency rescue. This would serve to quickly clear obstructions in asphyxiation emergencies, minimizing potential complications and life risks to the greatest extent possible.

While some airway obstruction removal devices already exist, such as airway suction devices, they work by creating negative pressure or a vacuum to suction and clear airway obstructions. Typically, an airway suction device includes a mask or tube connected to a suction apparatus, such as a manual pump or an electric suction machine. By using negative pressure or a vacuum, the airway suction device can help remove the obstruction from the airway of the individual experiencing asphyxiation. Portable airway suction devices often design the suction apparatus and the mask as an integrated unit. The rescuer places the entire device on the face of the individual experiencing asphyxiation and operates the device on their face to create a pressure difference, thereby clearing the obstruction.

However, existing airway obstruction removal devices have certain limitations.

Firstly, current portable airway suction devices are often designed with an integrated structure for generating negative pressure, making the overall dimensions relatively large, especially in terms of axial size. Since they can't be disassembled and are intended to be single-use products, they are not environmentally friendly. Secondly, some airway obstruction removal devices might pose unnecessary risks and complications. If poorly designed or improperly operated, they could cause further airway injuries, such as irritation or scratches to the throat, or even potentially lead to a perforation in the airway. Thirdly, some devices might generate excessive negative pressure or vacuum, which could result in complications like pneumothorax or lung injuries.

Therefore, there is a need for a new type of airway obstruction removal device to overcome the limitations of existing devices and offer a more efficient, portable, and easy-to-operate solution. This new device should be designed as simply as possible so that rescuers can quickly understand and operate it in emergency situations. Additionally, the device should be compact enough to be easily portable and storable.

SUMMARY

The objective of this disclosure is to provide a new type of airway obstruction removal device that is smaller in size, easier to transport and carry, and more convenient to use. This aims to overcome the limitations present in similar products based on existing technology. The device aims to offer a more effective solution with broader application scenarios and possibilities, allowing for easier management of emergency situations caused by airway obstruction.

In an embodiment, a respiratory obstruction removal device is provided. The respiratory obstruction removal device includes a face mask and a negative pressure generating device that exerts negative pressure on the face mask. The negative pressure generating device includes a grip portion, which includes a portion for handheld use, a top, and a bottom with an opening; an extendable tubular body, made of elastic material, featuring a variable-volume cavity with a hollow structure, one end of the extendable tubular body connected to the bottom of the grip portion; an annular interface, situated at another end of the extendable tubular body away from the grip portion, and equipped with a face mask interface for connecting to the face mask. The face mask includes an upper part configured to fit with the annular interface, a lower part fitted with a flexible annular cushion to conform to a face of a patient, and a connecting body linking the upper and lower parts. The respiratory obstruction removal device also includes a first one-way valve, situated within a channel that runs through the annular interface and connects the extendable tubular body with the face mask, in which an inlet end is in communication with the face mask, while an outlet end is in communication with an interior of the extendable tubular body, and the first one-way valve prevents the flow of air from the extendable tubular body into the face mask when the extendable tubular body is compressed. The first one-way valve allows air from the face mask to flow into the extendable tubular body when the extendable tubular body expands, specifically, the first one-way valve being placed on any component within the channel, including the mask, the extendable tubular body, or the annular interface. The respiratory obstruction removal device also includes a second one-way valve, situated in the grip portion, in which an outlet end is in communication with the external environment, while an inlet end is in communication with the extendable tubular body. The second one-way valve allows air to flow from the extendable tubular body to the external environment when the extendable tubular body is compressed; and the second one-way valve closes to prevent air from exiting the extendable tubular body when the extendable tubular body expands, and to block external air from entering, thereby maintaining a negative pressure environment within the extendable tubular body.

In one embodiment, the negative pressure generating device further includes a threaded interface, which is positioned at one end of the extendable tubular body adjacent and connected to the bottom of the grip portion, for threadedly engaging with the threaded bottom of the grip portion.

In one embodiment, an inner diameter of the threaded interface is smaller than an outer diameter of the grip portion, and the extendable tubular body in its normal extended state has an internal cavity size that can accommodate the grip portion when it is inverted inside it.

In one embodiment, a periphery of the annular interface is sealed to a periphery of one end of the extendable tubular body away from the grip portion and the upper part of the face mask includes a hollow connecting tube that tightly fits with the annular interface of the mask.

In one embodiment, the negative pressure generating device includes an annular interface with a uniform face mask interface, suitable for accommodating any mask among multiple sizes that have the same outer diameter for the hollow connecting tube.

In one embodiment, the negative pressure generating device further includes a sealing ring, used for sealing between the bottom of the grip portion and the threaded interface of the extendable tubular body.

In one embodiment, an elastic coefficient of the grip portion is greater than an elastic coefficient of a material of the extendable tubular body.

In one embodiment, the outer surface of the grip portion has an anti-slip structure.

In another embodiment, a respiratory obstruction removal device is provided that includes a face mask and a negative pressure generating device that is in communication with the face mask and operates under negative pressure. The negative pressure generating device includes a grip portion, which includes a portion for handheld use as well as a top and a bottom; an extendable tubular body, made of elastic material, featuring a variable-volume cavity with a hollow structure, one end of the extendable tubular body connected to the bottom of the grip portion; and an annular interface, situated at another end of the extendable tubular body away from the grip portion, and equipped with a face mask interface for connecting to the face mask. The face mask includes: an upper part configured to fit with the annular interface, a lower part fitted with a flexible annular cushion conform to a face of a patient, and a connecting body linking the upper and lower parts. The respiratory obstruction removal device also includes a first one-way valve situated in a channel that runs through the annular interface and connects the extendable tubular body with the face mask, in which an outlet end of the first one-way valve communicates with the interior of the extendable tubular body, and an inlet end is in communication with the face mask, specifically, the first one-way valve being placed on any component within the channel, including the mask, the extendable tubular body, or the annular interface; and a second one-way valve situated on the extendable tubular body, in which an outlet end of the second one-way valve communicates with the external environment, and an inlet end of the second one-way valve communicates with the interior of the extendable tubular body. When the extendable tubular body is compressed, the first one-way valve closes to prevent gas in the extendable tubular body from entering the face mask, while the second one-way valve allows air to flow from the extendable tubular body to the external environment; and when the extendable tubular body expands, the first one-way valve opens, allowing the gas inside the mask to flow into the extendable tubular body; the second one-way valve closes to prevent gas from flowing out of the extendable tubular body and external air from entering it, thereby maintaining a negative pressure environment within the extendable tubular body.

In one embodiment, the negative pressure generating device also includes a threaded interface, which is positioned at one end of the extendable tubular body adjacent and connected to the bottom of the grip portion, for threadedly engaging with the threaded bottom of the grip portion.

In one embodiment, the end for connection of the extendable tubular body that is adjacent to the bottom of the grip portion is sealed.

In one embodiment, an inner diameter of the threaded interface is smaller than an outer diameter of the grip portion, and the extendable tubular body in its normal extended state has an internal cavity that can accommodate the grip portion when it is inverted inside it.

In one embodiment, a periphery of the annular interface is sealed to a periphery of one end of the extendable tubular body that is far away from the grip portion, and the upper part of the face mask includes a hollow connecting tube that corresponds to and tightly fits with the face mask interface of the annular interface.

In one embodiment, the negative pressure generating device also includes a sealing ring, which is provided between the bottom of the grip portion and the threaded interface of the extendable tubular body to offer a seal.

In one embodiment, an outer surface of the grip portion has an anti-slip structure. In yet another embodiment, a respiratory obstruction removal device is provided that includes a face mask designed to cover a patient's face and a negative pressure generating device that exerts negative pressure on the face mask. The negative pressure generating device includes an extendable tubular body made of elastic material, consisting of a top, bottom, and a variable-volume cavity with a hollow structure in the middle; and an annular interface located at the bottom of the extendable tubular body, which is equipped with a face mask interface to connect with the face mask. The face mask includes: an upper part configured to fit with the annular interface, a lower part fitted with a flexible annular cushion to conform to a face of a patient, and a connecting body linking the upper and lower parts. The respiratory obstruction removal device also includes a first one-way valve, situated within the channel that runs though the annular interface and connects the extendable tubular body with the face mask, in which an inlet end is in communication with the face mask, while an outlet end is in communication with an interior of the extendable tubular body, and the first one-way valve prevents the flow of air from the extendable tubular body into the face mask when the extendable tubular body is compressed, and the first one-way valve allows air from the face mask to flow into the extendable tubular body when the extendable tubular body expands, specifically, the first one-way valve being placed on any component within the channel, including the mask, the extendable tubular body, or the annular interface; and a second one-way valve, situated on at least one of the extendable tubular body or annular interface in which an outlet end of the second one-way valve communicates with the external environment, while an inlet end of the second one-way valve is in communication with the extendable tubular body. The second one-way valve allows air to flow from the extendable tubular body to the external environment when the extendable tubular body is compressed; and the second one-way valve closes to prevent air from exiting the extendable tubular body when the extendable tubular body expands, and to block external air from entering, thereby maintaining a negative pressure environment within the extendable tubular body.

In one embodiment, a material and structure of the extendable tubular body are designed to ensure that its axial elastic coefficient is smaller than its elastic coefficient in any other direction.

In one embodiment, the top of the extendable tubular body is equipped with a handle or recessed handle, and the elasticity of this handle or recessed handle is less than the axial elasticity of the extendable tubular body.

In one embodiment, a periphery of the annular interface is sealed to a periphery of the bottom of the extendable tubular body, and the upper part of the face mask includes a hollow connecting tube that corresponds to and tightly fits with the face mask interface of the annular interface.

In one embodiment, the negative pressure generating device includes an annular interface with a uniform face mask interface, suitable for accommodating any mask among multiple sizes that have the same outer diameter for the hollow connecting tube.

In an embodiment, a respiratory obstruction removal device is provided that includes a face mask and a negative pressure generating device that exerts negative pressure on the face mask. The negative pressure generating device includes an extendable tubular body made of elastic material, consisting of a top, bottom, and a variable-volume cavity with a hollow structure in the middle; and an annular interface located at the bottom of the extendable tubular body, which is equipped with a face mask interface to connect with the face mask. The face mask includes: an upper part configured to fit with the annular interface, a lower part fitted with a flexible annular cushion to conform to a face of a patient, and a connecting body linking the upper and lower parts. The respiratory obstruction removal device also includes a first one-way valve situated in a channel that runs through the annular interface and connects the extendable tubular body with the face mask, in which an outlet end of the first one-way valve communicates with the interior of the extendable tubular body, and an inlet end is in communication with the face mask, specifically, the first one-way valve being placed on any component within the channel, including the mask, the extendable tubular body, or the annular interface; and a second one-way valve situated on the negative pressure generating device, in which an outlet end of the second one-way valve communicates with the external environment, and an inlet end of the second one-way valve communicates with the interior of the extendable tubular body When the extendable tubular body is compressed, the first one-way valve closes to prevent gas in the extendable tubular body from entering the face mask, while the second one-way valve allows air to flow from the extendable tubular body to the external environment; and when the extendable tubular body expands, the first one-way valve opens, allowing the gas inside the face mask to flow into the extendable tubular body; and the second one-way valve closes to prevent gas from flowing out of the extendable tubular body. The first one-way valve and the second one-way valve are oppositely arranged on the negative pressure generating device.

In one embodiment, a pull cord or handle is provided at the top of the extendable tube body.

In one embodiment, a periphery of the annular interface is sealed to a periphery of the bottom of the extendable tubular body, and the upper part of the face mask includes a hollow connecting tube that corresponds to and tightly fits with the face mask interface of the annular interface.

In one embodiment, the negative pressure generating device includes an annular interface with a uniform face mask interface, suitable for accommodating any mask among multiple sizes that have the same outer diameter for the hollow connecting tube.

Implementing the respiratory obstruction removal device of this disclosure has several beneficial effects, including but not limited to:

1. The device of this disclosure is designed to be detachable from its components, e.g., disassemblable, which distinguishes it from most of the disposable products currently on the market. This design is environmentally friendly and easier to maintain on a daily basis. In traditional products, if the device is not stored in a completely sealed manner, dust and insects may infiltrate the internal components. The inability to disassemble these traditional designs means that it's difficult to effectively clean such impurities. This could lead to contaminants hidden within the device entering the human body during use or blocking the airflow channels, thereby affecting its performance. Additionally, users often try out the product after purchasing to confirm its efficacy, but if the device can't be cleaned, this could raise hygiene concerns. Moreover, once a disposable product is used for respiratory obstruction removal, its non-disassemblable design means the entire product must be discarded, posing an environmental burden. Therefore, the present design allows for the product to be disassembled, making it convenient for daily cleaning and maintenance. After use, it can also be cleaned and disinfected for reuse, thereby extending the product's lifespan and cost-effectiveness while minimizing its environmental impact. Additionally, reducing the disposal rate of plastic is equivalent to reducing carbon emissions. To some extent, the use of this product accelerates the Earth's progress towards carbon neutrality. It features an eco-friendly design. At the same time, the detachable design of our removal device also has advantages over existing products in terms of disassembly and recycling. Thus, this product is more conducive to recycling, increasing the ease and possibility of circular reuse, and further aligning with the goal of carbon neutrality for the planet. This makes it more recyclable, increasing the ease and likelihood of recycling and further aligning with the global push for carbon neutrality.

2. The respiratory obstruction removal device of this disclosure is optimized with a detachable design, reducing the product's overall size. As a result, more units can be loaded into the same transport space, effectively reducing the number of required transportation vehicles. This design greatly enhances transport efficiency and cost-effectiveness. Not only does it lower logistics costs, but by reducing the number of vehicles needed, it also contributes positively to environmental protection by lowering exhaust emissions. Based on data up to the year 2021, carbon dioxide emissions from road traffic account for approximately 16%-18% of global carbon dioxide emissions. This indicates that road traffic is a significant source of global carbon dioxide emissions. Our product aims to reduce these emissions by decreasing the volume of goods, thereby reducing the number of transport vehicles needed. This, in turn, lowers the consumption and emission of carbon dioxide from automobile exhaust. Our disclosure continues the original intent of moving towards global carbon neutrality by reducing the carbon footprint of vehicles.

3. The reduction in product size offers greater portability for the user. Users can conveniently place the product in a personal bag or the storage compartment of a car's front seat. This design substantially increases the frequency with which users carry the device with them. In the event of a choking emergency, the user can immediately use the device to clear the respiratory obstruction, allowing for quicker and more effective emergency response.

DETAILED DESCRIPTION

To facilitate an understanding of this disclosure, a more comprehensive description will be provided below with reference to the relevant drawings. The drawings present typical embodiments of this disclosure. However, it should be understood that the disclosure can be implemented in many different forms and is not limited to the embodiments described herein. Rather, these embodiments are provided to make the disclosure more thorough and comprehensive.

Unless otherwise defined, all technical and scientific terms used herein have the same meaning as commonly understood by those of ordinary skill in the art to which this disclosure belongs. The terms used in the description of the disclosure herein are for the purpose of describing particular embodiments only and are not intended to be limiting of the disclosure.

In an embodiment, the grip portion is connected to the extendable tubular body, forming an internal seal. A sealing ring is placed at the connection point to enhance its sealing performance. Because the inner diameter of the threaded interface of the extendable tubular body is smaller than the outer diameter of the grip portion, and the extendable tubular body in its normally extended state has a cavity size that can accommodate the grip portion when inverted, the volume is convenient for carrying and transportation. The outer surface of the grip portion features an anti-slip structure, ensuring that rescuers won't make operational errors even under stressful, emergency conditions.

In some embodiments, the mask consists of an upper part, connecting body, and lower part. The upper part can take various forms to fit with the annular interface, ensuring that the gas from the face mask can flow into the extendable tubular body through the first one-way valve located in the channel that runs through the annular interface and connects the extendable tubular body and the mask. The lower part ensures a comfortable, sealed contact with a patient's face, forming a sealed face mask cavity. According to one aspect of the disclosure, the grip portion can either be a part that communicates with the extendable tubular body or can be located on the exterior of the extendable tubular body. Both configurations aid the user in stretching and compressing the extendable tubular body, ensuring that the face mask connected through the annular interface can remove respiratory obstructions through negative pressure.

Figure 5:
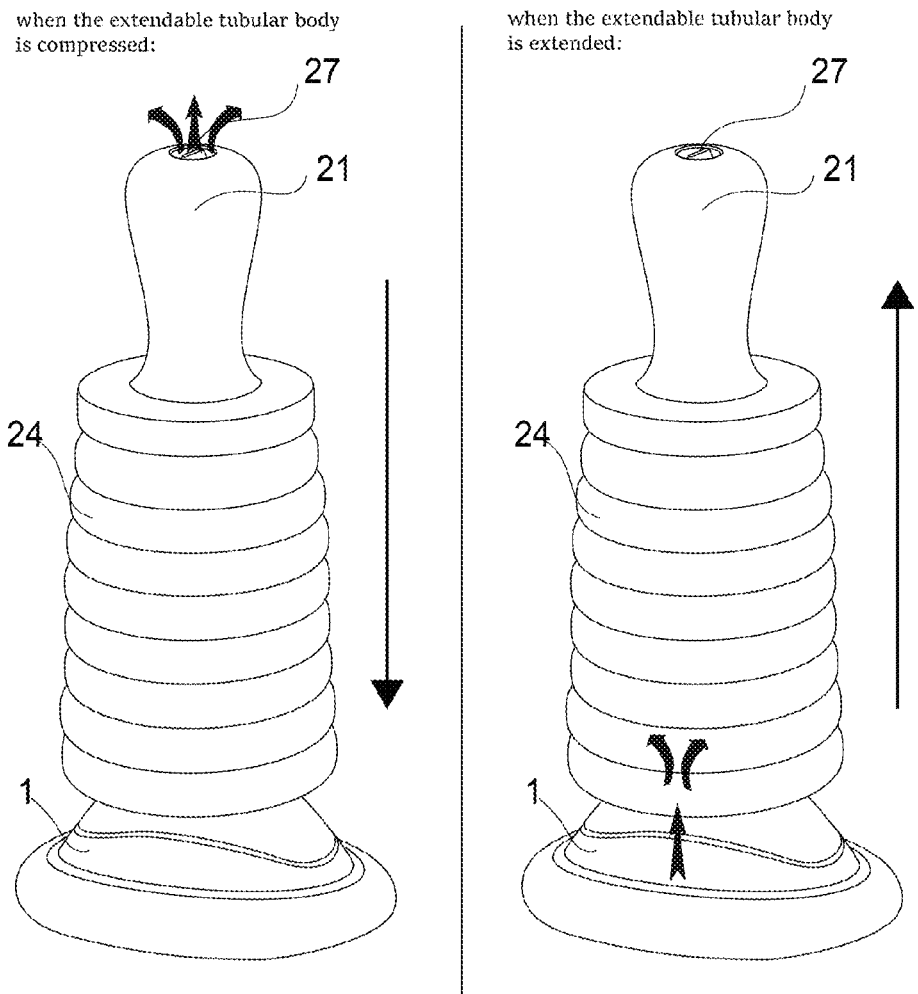
FIG. 5 is a schematic diagram of a direction of gas flow in a respiratory obstruction removal device in accordance with another embodiment.

In some embodiments, the first and second one-way valves function as the inhalation and exhalation valves, respectively. When the extendable tubular body is compressed by manipulating the grip portion, the first one-way valve prevents the gas inside the extendable tubular body from flowing into the face mask, while the second one-way valve allows the gas inside the extendable tubular body to be released to the external environment. Conversely, when the extendable tubular body is stretched by the grip portion, the first one-way valve allows the gas inside the face mask to flow into the extendable tubular body. The second one-way valve closes to prevent the gas inside the extendable tubular body from flowing out and to block external airflow from entering the extendable tubular body, thereby maintaining a negative pressure environment within the extendable tubular body. The directional flow of the air is illustrated in FIG. 5. According to one aspect of the application, the first and second one-way valves can be located within the channel that runs through the annular interface and connects the extendable tubular body with the face mask and on the top of the hollow grip portion, respectively. Alternatively, the second one-way valve can be positioned in other locations on the negative pressure generating device, excluding the top of the hollow grip portion. In this configuration, the other end of the negative pressure generating device could either be a hollow grip portion with a threaded combination, a non-hollow grip portion, or a sealed flat surface without a grip portion. Any of these configurations would be equally effective in removing respiratory obstructions.

In this disclosure, the annular interface has a uniform size at the connection points with both the face mask and the extendable tubular body, which allows for compatibility with face masks of various shapes and sizes, as long as each type of face mask has a hollow connecting tube with the same outer diameter. This enables different masks to fit the same negative pressure generating device, thereby enhancing its versatility and reducing supply chain costs. The negative pressure generating device is in communication with the face mask through a channel that runs through the annular interface. The first one-way valve located at the connection point on the annular interface achieves unidirectional airflow between the negative pressure generating device and the face mask. The face mask provides a hollow connecting tube, corresponding to the connection point on the annular interface. This design ensures that the negative pressure generating device structurally connects to the face mask, forming a unified whole.

In using the respiratory obstruction removal device provided by the implementation of this disclosure, start by assembling the face mask with the negative pressure generating device. Place the flexible annular cushion of the face mask around the mouth of the choking patient and ensure it fits against their face so that a passageway is formed between the face mask and their airway. Then, hold the face mask with one hand to maintain a seal between the mask and the face while holding the grip portion of the negative pressure generating device with the other hand. Perform axial compressions and extensions of the device repetitively to quickly extract any obstruction from the patient's airway through the created negative pressure. During the compression (axial size reduction) of the extendable tubular body, made of elastic material and layered structure, the gas within the extendable tubular body is expelled to the external environment via the second one-way valve and cannot enter the patient's airway through the first one-way valve. During the expansion (axial size increase) of the extendable tubular body, the volume of the tubular body's cavity increases. The second one-way valve prevents external air from flowing into the air storage cavity, thus creating a negative pressure environment inside the cavity. This means that the air pressure inside the cavity is lower than the air pressure in the patient's airway, allowing for the airway pressure to exert an outward force on the obstruction, thereby extracting and clearing it of the obstruction.

In summary, by using the removal device, a simple repetitive stretching action may be used to quickly and effectively assist a patient experiencing respiratory obstruction due to choking. This provides a fast and effective rescue method when the Heimlich maneuver can't be effectively implemented. Moreover, if one finds themselves choking with an obstructed airway and no one else is around to help, the removal device can be used for effective self-rescue.

Embodiment 1

This embodiment provides a respiratory obstruction removal device that is easy to carry and transport. The embodiment includes a three-dimensional combined schematic, a cross-sectional structural schematic, a principle schematic, and an innovation expression diagram, as referenced in FIGS. 1, 3, 4-7, and 12. The respiratory obstruction removal device shown in the embodiment consists of two parts: a face mask 1 and a negative pressure generating device 2. The face mask 1 is designed to cover at least the cheeks of a person, while the negative pressure generating device 2 is assembled and connected to the face mask 1 and provides negative pressure. The negative pressure generating device 2 sequentially includes a grip portion 21, an extendable tubular body 24, and an annular interface 25. A sealing ring 22 may also be present between the grip portion 21 and the extendable tubular body 24. Because the grip portion 21 and the extendable tubular body 24 may be connected via threads, the sealing ring 22 is used to create a seal between them. A periphery of the annular interface 25 is sealed to a periphery of one end of the extendable tubular body 24 away from the grip portion 21. The negative pressure generating device 2 is connected to the face mask 1 through the annular interface 25. During use, the face mask 1 can be placed over a patient's face to connect to the mouth and nose (respiratory organs) of the individual. The face mask 1 is also connected to the negative pressure generating device 2 via the annular interface 25. The latter is configured to apply negative pressure to the face mask 1 and, through the face mask, removes the obstructive material from the person's airway, thereby clearing it.

Figure 1:
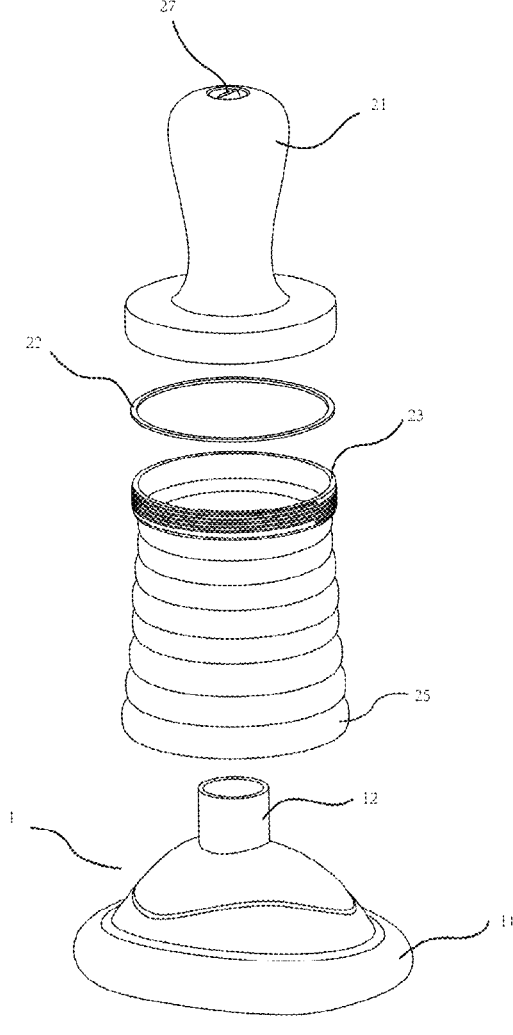
FIG. 1 is an exploded schematic diagram of a respiratory obstruction removal device in accordance with an example embodiment.
Figure 3:
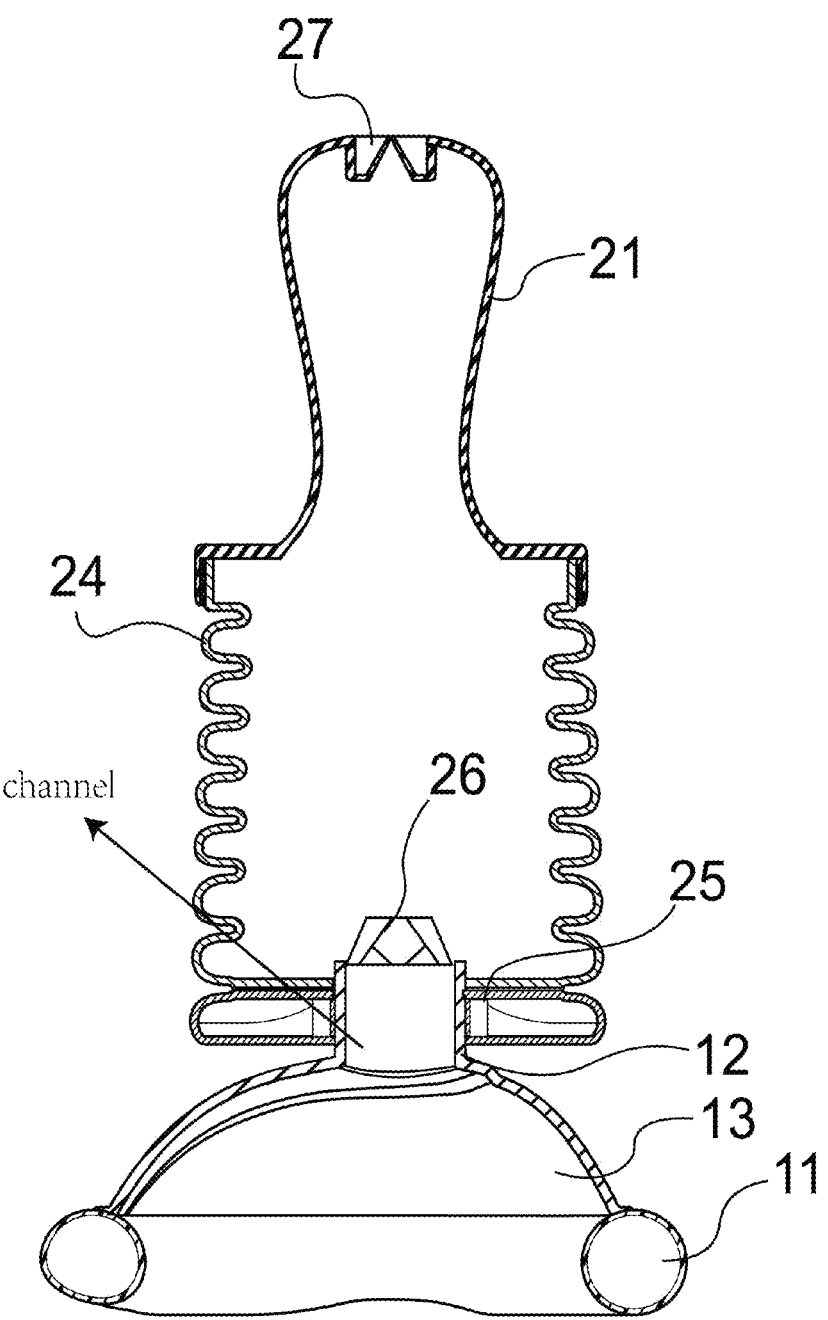
FIG. 3 is a schematic cross-sectional view of the respiratory obstruction removal device in FIG. 1.

As shown in FIGS. 1 and 3, the top end of the grip portion 21 may be equipped with a second one-way valve 27. The outlet end of this valve is in communication with the external environment, while the inlet end communicates with the extendable tubular body 24. The bottom of the extendable tubular body 24 features an annular interface 25 for connecting to the face mask 1. A first one-way valve 26 is located within the channel that runs through the annular interface 25 and connects the extendable tubular body 24 with the face mask 1 (that is, the channel is a pathway for air to flow from the face mask into the extendable tubular body when the extendable tubular body 24, the annular interface 25, and the face mask 1 are connected). That is, the first one-way valve 26 can be positioned within the channel of the face mask 1. Simultaneously, the face mask 1 includes a hollow connecting tube 121 that fits with the annular interface 25 and is inserted upwards into the annular interface 25 to achieve a connection between the annular interface 25 and the face mask 1. The face mask 1 and the annular interface 25 are currently connected through their frictional force. In other implementations, they can also be connected by adhesive, welding, or snap-fit mechanisms. The inlet end of the first one-way valve 26 communicates with the face mask 1, and the outlet end communicates with the interior of the extendable tubular body 24. This setup enables the unidirectional flow of air from the face mask 1 through the hollow connecting tube 121 and the first one-way valve 26 into the extendable tubular body 24. This prevents air in the extendable tubular body 24 from escaping back into the face mask 1 through the annular interface 25 when the extendable tubular body 24 is compressed. When the extendable tubular body 24 is extended again, negative pressure is generated within it. Under this negative pressure, the face mask 1 draws obstructive material from the human airway through the first one-way valve 26 into the extendable tubular body 24, which is then expelled. In some other embodiments, the outer surface of the grip portion 21 features an anti-slip structure. This enhances the frictional force of the grip portion 21, making it less likely for the hand to slip when operating the grip portion 21, thereby facilitating the up-and-down movement of the extendable tubular body 24. This added convenience in compressing and extending the extendable tubular body 24 improves the efficiency of the respiratory obstruction removal device in clearing airway obstructions. At the same time, in order to provide better gripping, an elastic modulus of the grip portion 21 can be at or between 0.13-3.5 GPa, and an elastic coefficient of the grip portion 21 is greater than an elastic coefficient of the extendable tubular body 24 (that is, the gripping part 21 can be constructed to be more rigid than the expandable tubular body 24 through the design of materials, wall thickness, and structure).

The extendable tubular body 24 is made of elastic material and features multiple continuously foldable walls on its surface. This allows the tube to be axially extendable. The cross-section of this tubular body can be circular, as a circular shape is easier to manufacture. The extendable tubular body 24 has two states within the negative pressure generating device 2: a normally extended state and a compressed state when pressure is applied. The direction of compression and extension for the extendable tubular body 24 aligns with the length direction of the grip portion 21. This means that by manually gripping the grip portion 21, the extendable tubular body 24 can be stretched and compressed, thereby changing its internal pressure and facilitating the removal of airway obstructions through the face mask 1. To ensure the expandable tubular body 24 can be smoothly stretched and compressed, a material and structure of the extendable tubular body 24 are designed to ensure that an axial elastic coefficient is smaller than an elastic coefficient in any other direction (i.e., its ability to deform axially is greater than in other directions).

Figure 6:
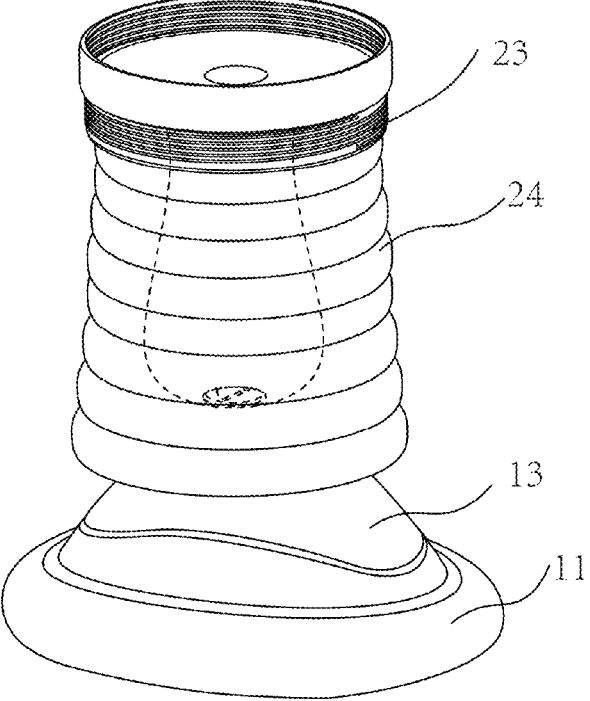
FIG. 6 is a schematic diagram of an inverted grip portion in an embodiment.
Figure 7:
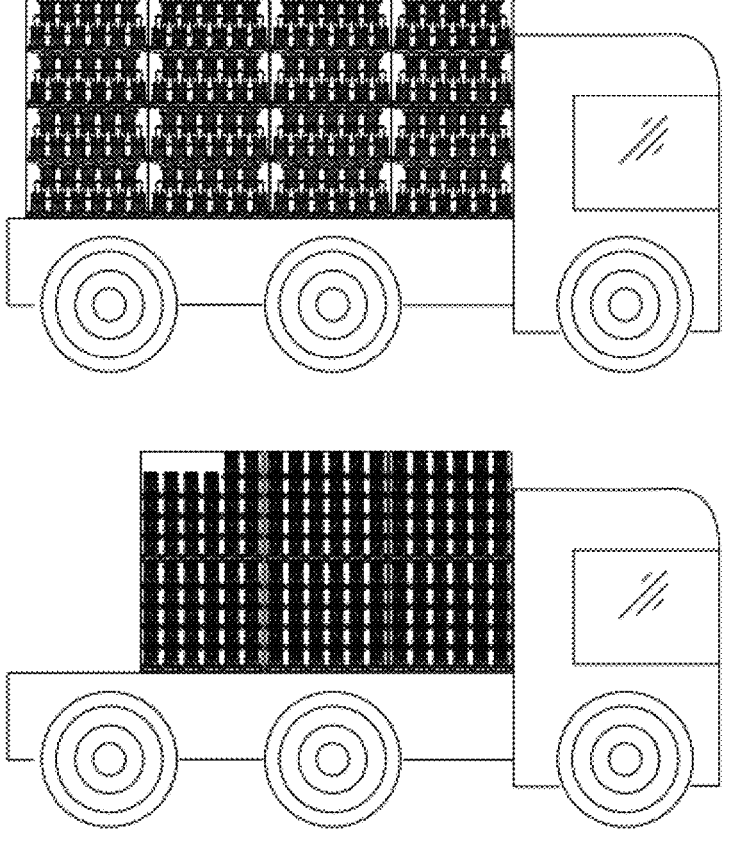
FIG. 7 is a schematic diagram of the transportation of the respiratory obstruction removal device when the grip portion is inverted, in accordance with an embodiment.
Figure 13:
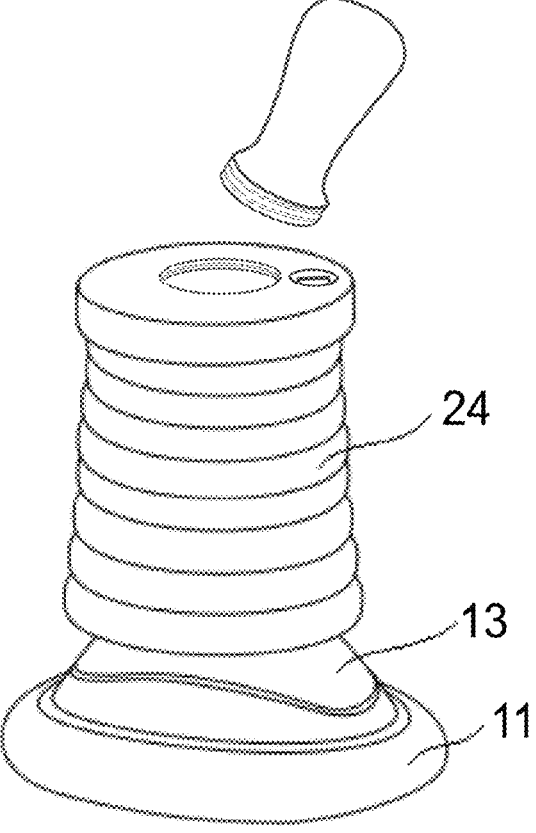
FIG. 13 is a disassembly schematic diagram of a grip portion in another form of in one embodiment.

The internal space of the extendable tubular body 24 is formed by its pleated sections and connects to the hollow structure of the grip portion 21 through a threaded interface 23, collectively forming a variable volume cavity. Normally, when the extendable tubular body 24 is in its extended state, it also has an internal cavity that can accommodate the middle and upper parts of the grip portion 21. As shown in FIG. 5, the outer circumference of the grip portion 21 can be at or between 80 to 720 millimeters, and the inner edge of the annular interface 25 can be at or between 30 to 360 millimeters. This design allows the grip portion 21 to be inverted and placed inside the extendable tubular body 24 after unscrewing them apart. With radial size matching, the grip portion 21 won't fall out from one end of the extendable tubular body 24 adjacent to the annular interface 25, ensuring stable placement within the extendable tubular body 24. This design also reduces the overall size of the respiratory obstruction removal device, making it more convenient to carry and transport. During transport, the grip portion 21 can be inverted and stored inside the cavity of the extendable tubular body 24. This makes the bottom of the grip portion 21 become the top of the device. Since the bottom of the grip portion 21 is flat, it facilitates neat and orderly stacking during transport, as shown in FIG. 6. This also minimizes the space occupied by the device, allowing for the transportation of more units in the same amount of space. In another variation, as shown in FIG. 13, the grip portion 21 can also be set as a separate handle. As shown in FIGS. 6-7, the end of the extendable tubular body 24 that is far away from the grip portion 21 features the annular interface 25, which is used for connecting the extendable tubular body 24 and the face mask 1. The face mask 1 includes an upper part 12, a lower part 11, and a connecting body 13. The upper part 12 fits with the annular interface 25, the lower part 11 is a flexible annular cushion that ensures the face mask 1 fits against the face of a patient, and the connecting body 13 links the upper and lower parts. For easier manufacturing, all three components can be molded into a single piece.

In other embodiments, the connection between the grip portion 21 and the extendable tubular body 24 can also be a snap-fit connection, a zipper connection, or other types of connections.

Figure 12:
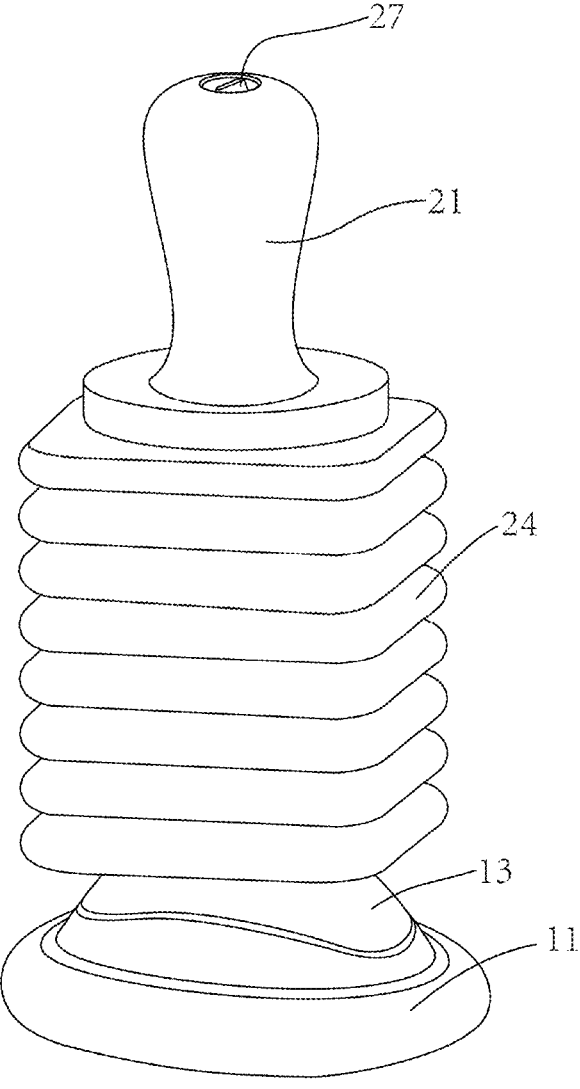
FIG. 12 is a schematic diagram of a respiratory obstruction removal device using an extendable tubular body of a different shape in yet another embodiment.

To enhance the seal of the variable cavity formed by the extendable tubular body 24 and the grip portion 21, the negative pressure generating device 2 may also include a sealing ring 22. This ring is placed between the extendable tubular body 24 and the grip portion 21. The sealing ring 22 is annular in shape and made of food-grade, safe, elastic material. The inner and outer diameters of the sealing ring 22 correspond to the diameters of the interface end surfaces of the extendable tubular body 24 and the bottom of the grip portion 21, respectively. The thickness of the sealing ring 22 can be at or between 0.1 to 1 millimeters. During use, the ring is placed between the threaded end face of the grip portion 21 and the threaded interface 23 of the extendable tubular body 24. After tightening them together, the sealing ring is clamped between the two end faces, ensuring that the cavity formed by the hollow grip portion 21 and the extendable tubular body 24 is sealed at the threaded connection. This ensures that the extendable tubular body 24 is airtight with the exterior when the grip portion 21 is held and pulled, thus maintaining the airtightness of the entire clearing device. In other embodiments, as shown in FIG. 12, the cross-section of the extendable tubular body 24 can also take other shapes, such as triangular, polygonal, or elliptical shapes.

The upper part 12 of the mask 1 includes a hollow connecting tube 121, which fits with the annular interface 25 of the face mask interface. To accommodate different user groups, the face mask 1 can be designed in various sizes (i.e. the lower part 11 can be designed to accommodate different sizes—large, medium, and small—to fit various groups of people) with the same outer diameter for the hollow connecting tube 121. Correspondingly, the annular interface 25 can come in various sizes with corresponding identical inner diameters at the center to connect with the face mask. That is, the negative pressure generating device 2 includes an annular interface 25 with a unified mask interface, used to match any one of the face masks 1 with various sizes and the same outer diameter of the hollow connection tube 121; in other words, aside from the standardized size at the connection point between the hollow connecting tube 121 and the annular interface 25 center, other parts of the face mask 1 can come in any size. This allows for the replacement of face masks of different sizes in different practical scenarios. As a result, the respiratory obstruction removal device of this disclosure can adapt to the facial dimensions of different patients, thereby broadening its range of applicability.

In summary, the respiratory obstruction removal device in this embodiment includes a grip portion 21, which consists of a portion for handheld use, a top, and a bottom with an opening. The respiratory obstruction removal device also includes an extendable tubular body 24, made of elastic material, with a hollow structure forming a variable-volume cavity. One end of the tubular body 24 is connected to the bottom of the grip portion 21. An annular interface 25 is set at the other end of the extendable tubular body 24, far away from the grip portion 21. This annular interface 25 includes a mask interface for connecting to the face mask 1.

The face mask 1 comprises: an upper part 12, designed or configured to fit with the annular interface 25; a lower part 11, featuring a flexible annular cushion to ensure that the face mask fits tightly against the human face; and a connecting body 13, for connecting the upper and lower parts.

Figure 4A:
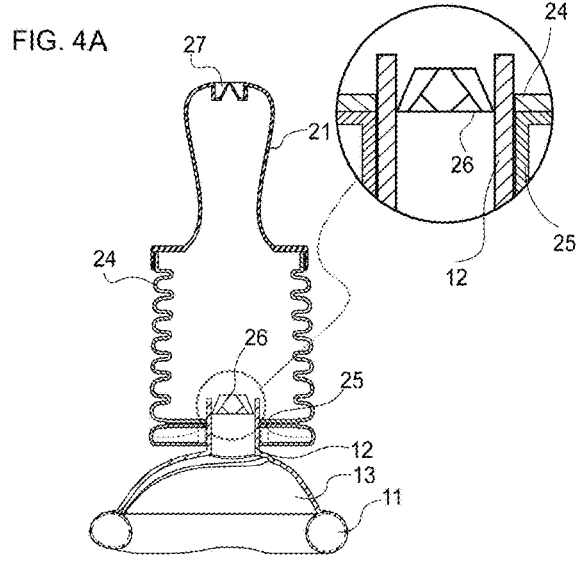
FIGS. 4A, 4B, 4C are schematic diagrams of a first one-way valve positioned within a channel that runs through an annular interface and connects an extendable tubular body and a face mask, in accordance with an example embodiment.

The respiratory obstruction removal device also includes: a first one-way valve 26, placed in the channel that runs through the annular interface 25 and connects the extendable tubular body 24 with the face mask 1. Specifically, the first one-way valve 26 is located in the face mask 1 section of the channel (as shown in FIG. 4A). The inlet end communicates with the face mask 1, and the outlet end communicates with the interior of the extendable tubular body 24. When the extendable tubular body 24 is compressed, the first one-way valve 26 prevents the gas inside from flowing into the face mask 1. When the tubular body 24 expands, the first one-way valve 26 allows gas from inside the face mask 1 to flow into the extendable tubular body 24.

A second one-way valve 27 is set in the grip portion 21, with the outlet end communicating with the external environment and the inlet end communicating with the extendable tubular body 24. When the extendable tubular body 24 is compressed, the second one-way valve 27 allows the airflow inside the extendable tubular body 24 to flow out. When the extendable tubular body 24 expands, the second one-way valve 27 closes to prevent the flow of air from the interior of the extendable tubular body 24 to the external environment, as well as the flow of external air into the extendable tubular body 24, thereby maintaining a negative pressure environment inside the extendable tubular body 24.

Embodiment 2

Figure 4B:
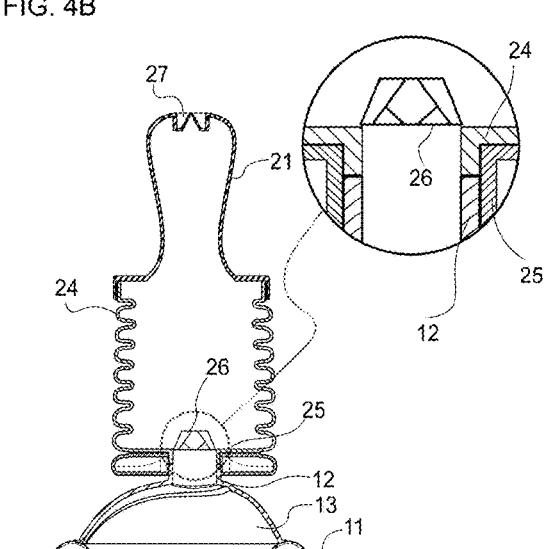
Figure 4C:
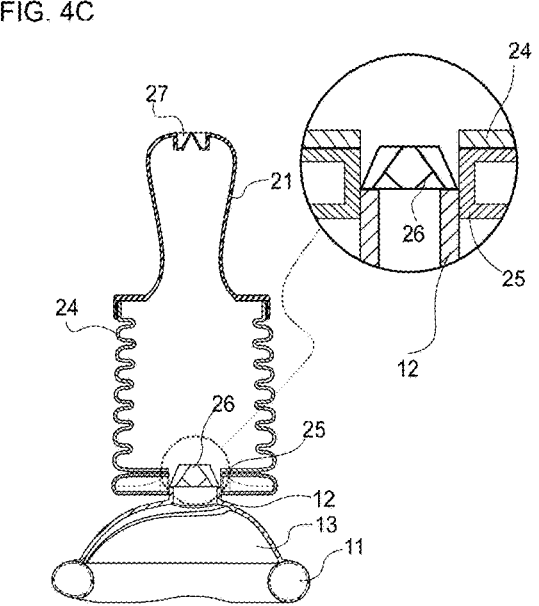

This embodiment presents a respiratory obstruction removal device that is convenient to carry and transport, as shown in FIGS. 4A, 4B, 4C, which illustrate a cross-sectional structural schematic diagram of the respiratory obstruction removal device. The difference between this embodiment and Embodiment 1 lies in the positioning of the first one-way valve 26. In this embodiment, the first one-way valve 26 is located in the channel that runs through the annular interface 25 and connects the extendable tubular body 24 and the face mask 1. Specifically, the first one-way valve 26 can be situated either on the channel of the annular interface 25 (as shown in FIG. 4C) or on the extendable tubular body 24 (as shown in FIG. 4B), offering a variety of implementation methods. This respiratory obstruction removal device includes a grip portion 21, which consists of a portion for handheld use, a top, and a bottom with an opening. The respiratory obstruction removal device also comprises an extendable tubular body 24 made from an elastic material, featuring a hollow structure that forms a variable-volume cavity. One end of this extendable tubular body 24 is connected to the bottom of the grip portion 21. The respiratory obstruction removal device further includes an annular interface 25 located at another end of the extendable tubular body 24 far away from the grip portion 21. The annular interface is provided with a face mask interface for connecting to the face mask 1. The face mask 1 consists of: an upper part 12, configured to fit with the annular interface 25; a lower part 11, featuring a flexible annular cushion to ensure a snug fit against the human face; and a connecting body 13 to join the upper and lower parts. The respiratory obstruction removal device also includes a first one-way valve 26, which is positioned within the channel that runs through the annular interface 25 and connecting the extendable tubular body 24 with the face mask 1. Specially, the first one-way valve 26 can either be situated within the channel of the annular interface 25 (referring to FIG. 4C) or the same channel of the extendable tubular body 24 (referring to FIG. 4B). The inlet end communicates with the face mask 1, and the outlet end communicates with the interior of the extendable tubular body 24. When the extendable tubular body 24 is compressed, the first one-way valve 26 prevents the air inside the extendable tubular body 24 from flowing into the face mask 1. Conversely, when the extendable tubular body 24 expands, the first one-way valve 26 allows the air from inside the face mask 1 to flow into the extendable tubular body 24. The respiratory obstruction removal device also includes a second one-way valve 27 positioned in the grip portion 21. Its outlet end communicates with the external environment, and its inlet end is connected to the extendable tubular body 24. When the extendable tubular body 24 is compressed, this second one-way valve 27 allows the air inside the extendable tubular body 24 to flow to the external environment. When the extendable tubular body 24 expands, the second one-way valve 27 closes, preventing air inside the extendable tubular body 24 from flowing to the external environment, and then blocking air from the external environment entering into the extendable tubular body 24, thereby maintaining a negative pressure environment within the extendable tubular body 24.

Embodiment 3

Figure 2:
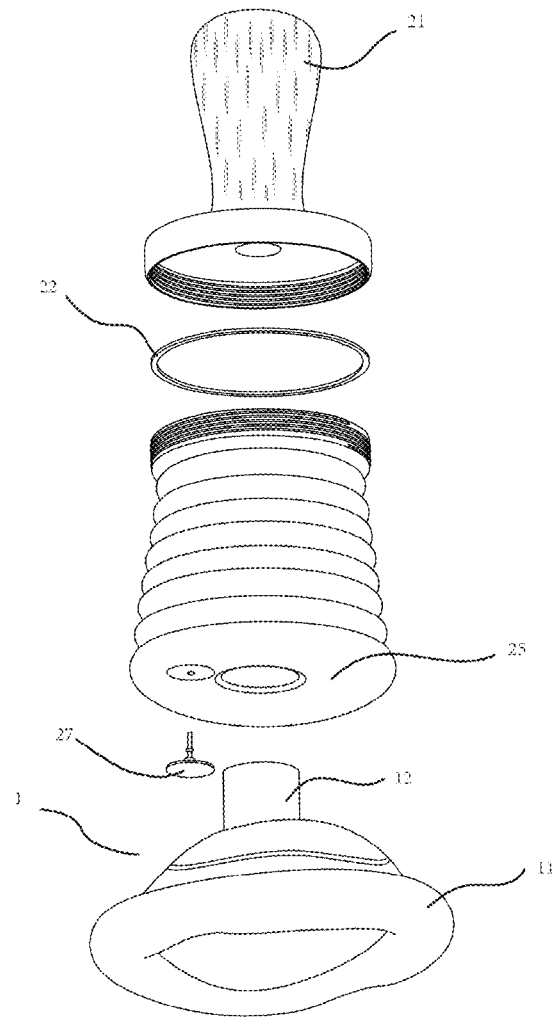
FIG. 2 shows an exploded schematic diagram of a respiratory obstruction removal device, featuring an anti-slip design on the grip portion, in accordance with an another embodiment.
Figure 8:
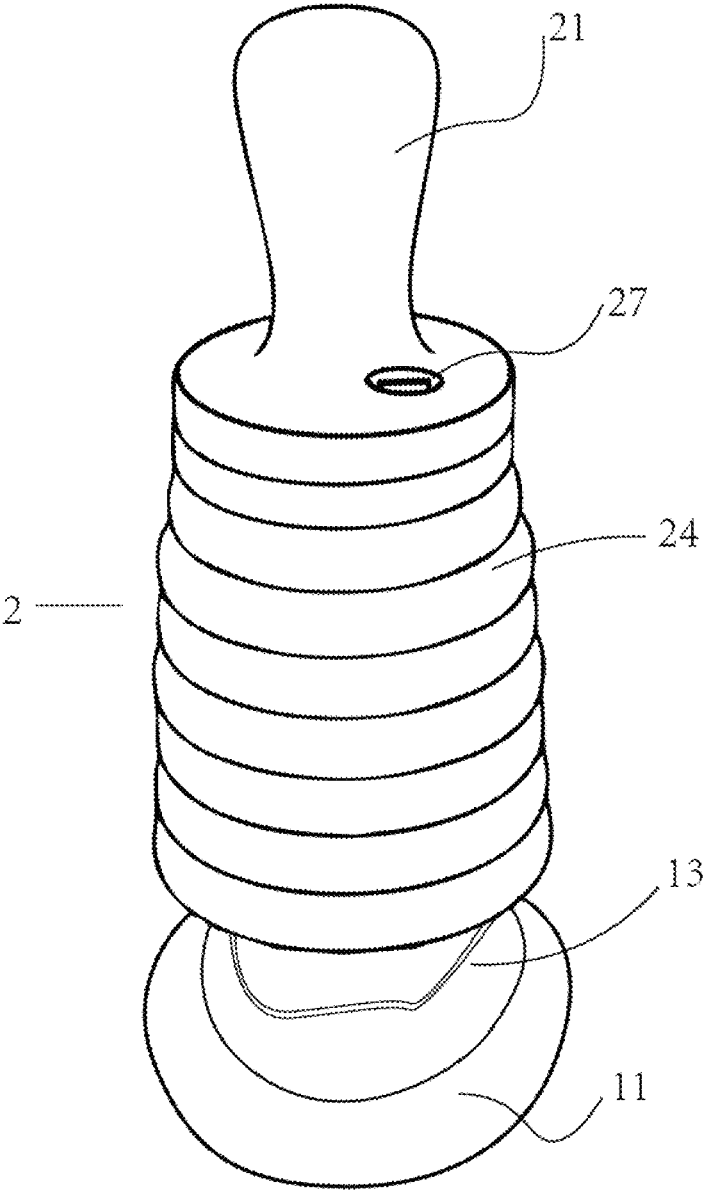
FIG. 8 is a schematic diagram of the second one-way valve provided on the extendable tubular body in another embodiment.

This embodiment offers a respiratory obstruction removal device that is convenient to carry and transport, as referenced in FIGS. 2 and 8 which illustrate three-dimensional schematic diagrams of the respiratory obstruction removal device. The difference between this embodiment and Embodiment 1 lies in the placement of the second one-way valve 27. Specifically, the second one-way valve 27 can be situated at the bottom of the annular interface 25 or on the extendable tubular body 24. To improve the stability of the obstruction removal device during use, the outer surface of the grip portion 21 features an anti-slip structure. This enhances the friction between the hand and the grip portion 21, reducing the chance of slippage, particularly when the hand is sweaty. This improved grip aids in the ease of moving the extendable tubular body 24 up and down for compression and expansion, thus increasing the efficiency of the device in removing respiratory obstructions from the patient. Specifically, in other embodiments, the anti-slip structure could be made of materials like silicone or employ raised and recessed features to increase the friction between the palm and the grip portion 21.

In this embodiment, the respiratory obstruction removal device includes a grip portion 21, which consists of a portion for handheld use, a top, and a bottom with an opening. The device also features an extendable tubular body 24, made of elastic material, with a hollow structure forming a variable-volume cavity. One end of the extendable tubular body 24 is connected to the bottom of the grip portion 21. The obstruction removal device also includes an annular interface 25 positioned at another end of the extendable tubular body 24 that is far away from the grip portion 21. This annular interface 25 includes a face mask interface for connecting to the face mask 1. The face mask 1 consists of an upper part 12, which fits with the annular interface 25, and a lower part 11, featuring a flexible annular cushion that fits against the face of a patient. There's also a connecting body 13 that links the upper and lower parts of the face mask.

Additionally, the device includes a first one-way valve 26, situated within the channel that runs through the annular interface 25 and connects the extendable tubular body 24 with the face mask 1. The inlet end of the first one-way valve communicates with the face mask 1, and the outlet end communicates with the interior of the extendable tubular body 24. When the extendable tubular body 24 is compressed, the first one-way valve 26 prevents the gas within the extendable tubular body 24 from entering the face mask 1. When the extendable tubular body 24 expands, the first one-way valve allows the gas inside the face mask 1 to enter the extendable tubular body 24.

The device also features a second one-way valve 27, positioned on at least one of the extendable tubular body 24 or the annular interface 25. The outlet end of the second one-way valve communicates with the exterior, while the inlet end communicates with the extendable tubular body 24. When the extendable tubular body 24 is compressed, the second one-way valve 27 allows the gas inside the extendable tubular body 24 to flow to the external environment. When the extendable tubular body 24 expands, the second one-way valve 27 closes to prevent the gas inside the extendable tubular body 24 from flowing to the external environment and to stop the external air from flowing in, thereby maintaining a negative pressure environment within the extendable tubular body 24.

By not placing the second one-way valve 27 on the top of the grip portion 21, the design avoids the risk of the palm inadvertently blocking the second one-way valve 27 while gripping the grip portion 21 and compressing the extendable tubular body 24, thereby improving the efficiency of the device.

Embodiment 4

Figure 9:
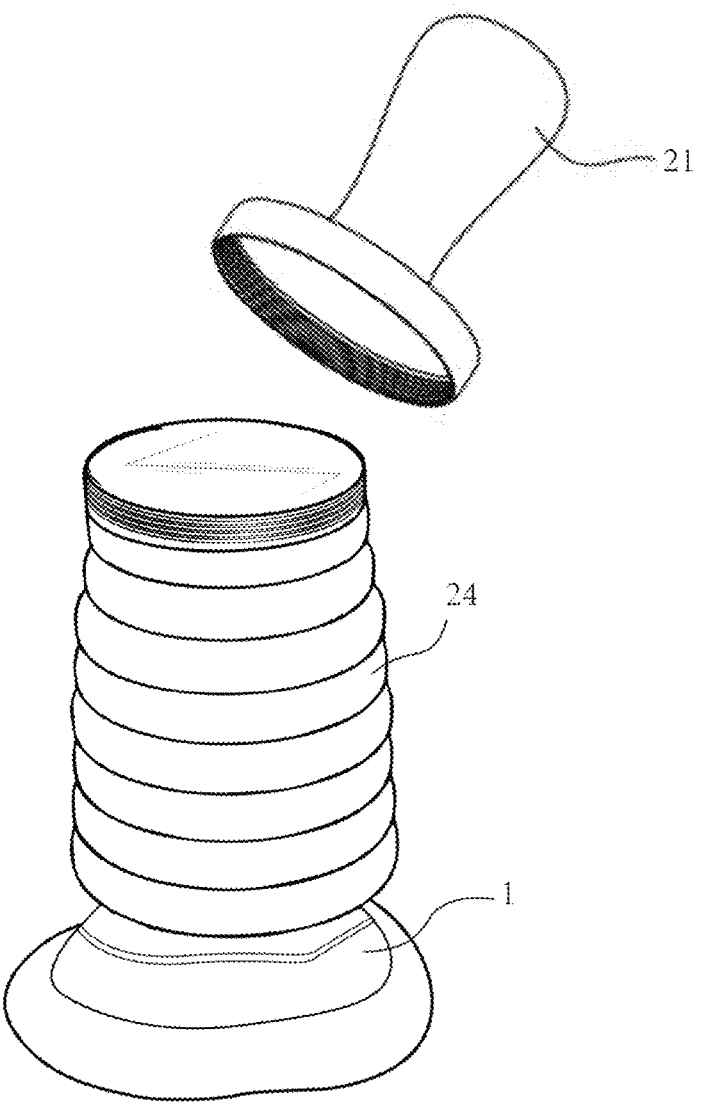
FIG. 9 is a schematic diagram of a respiratory obstruction removal device where an end for connection of an extendable tubular body that is adjacent and connected to a bottom of a grip portion is sealed, in accordance with yet another embodiment.

In this embodiment, a respiratory obstruction removal device that easy to carry and transport is provided, as shown in FIG. 9, which is a three-dimensional schematic diagram of the respiratory obstruction removal device. The key difference from the first embodiment lies in the way the extendable tubular body 24 is connected to the grip portion 21: one end of the extendable tubular body 24 close to the bottom of the grip portion 21 is sealed, and the extendable tubular body 24 connects to the grip portion 21 through a threaded interface, allowing for a rotating, meshed connection. The grip portion itself can be either hollow or solid. The respiratory obstruction removal device in this embodiment includes a grip portion 21, which consists of a part for handheld use, a top, and a bottom with an opening. It also features an extendable tubular body 24, made of elastic material, with a hollow structure forming a variable-volume cavity. One end of this extendable tubular body 24 is connected to the bottom of the grip portion 21. The respiratory obstruction removal device also consists of an annular interface 25 positioned at the other end of the extendable tubular body 24, far from the grip portion 21. This annular interface 25 includes a face mask interface for connection to face mask 1. The face mask 1 comprises an upper part 12, configured to fit with the annular interface 25, and a lower part 11 featuring a flexible annular cushion to fit against the face of a patient. A connecting body 13 links the upper and lower parts of the face mask.

The device also includes a first one-way valve 26, situated within the channel that runs through the annular interface 25 and connects the extendable tubular body 24 with the face mask 1. The inlet end of the first one-way valve communicates with the face mask 1, and the outlet end communicates with the interior of the extendable tubular body 24. When the extendable tubular body 24 is compressed, the first one-way valve 26 prevents air inside it from flowing into the face mask 1. When the extendable tubular body 24 expands, the first one-way valve 26 allows air from inside the face mask 1 to flow into the extendable tubular body 24. Furthermore, the device includes a second one-way valve 27, located either on the extendable tubular body 24 or the annular interface 25. The outlet end of the second one-way valve 27 communicates with the external environment, and the inlet end communicates with the interior of the extendable tubular body 24. When the extendable tubular body 24 is compressed, the second one-way valve 27 allows the air within the extendable tubular body 24 to flow outwards. When the extendable tubular body 24 expands, the second one-way valve 27 closes to stop air from flowing out and prevents external air from flowing in the extendable tubular body 24, thereby maintaining a negative pressure environment within the extendable tubular body 24.

Embodiment 5

Figure 10:
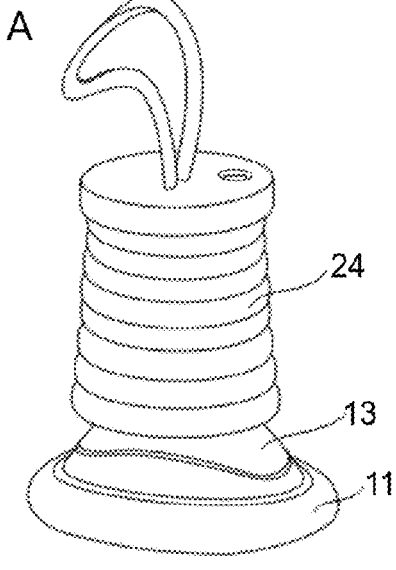
FIG. 10 is a schematic diagram of various forms of a respiratory obstruction removal device without a grip portion in accordance with various embodiments.
Figure 10:
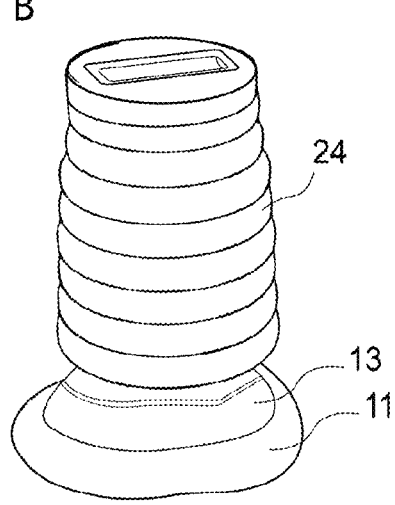
Figure 10:
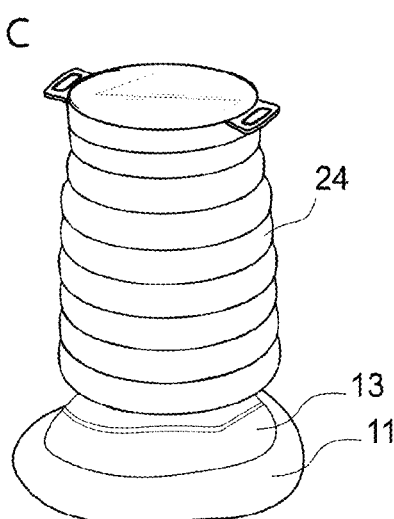

This embodiment presents a portable respiratory obstruction removal device that is convenient to transport, as shown in FIG. 10, which illustrates three-dimensional schematic diagrams of the device. The key difference in this embodiment as shown in FIG. 10 compared to the first one is that the negative pressure generating device 2 does not feature a grip portion 21. Instead, it solely comprises an extendable tubular body 24 and an annular interface 25. The sealed top of the extendable tubular body 24 includes a handle that can take various forms such as a pull cord, a recessed handle, handles on both sides, or other forms conducive to applying force. This design allows the user to easily switch between compressing and extending the extendable tubular body 24, thereby varying its internal volume. Additionally, the negative pressure generating device 2 is equipped with a second one-way valve 27. The respiratory obstruction removal device of this embodiment includes an extendable tubular body 24 made of elastic material, forming a hollow, variable-volume cavity. The annular interface 25 is situated at the bottom of this extendable tubular body and features a face mask interface for connecting to the face mask 1. The face mask 1 consists of an upper part 12, which fits with the annular interface 25, a lower part 11, which includes a flexible annular cushion to fit against the patient's face, and a connecting body 13 linking the upper and lower parts of the face mask. Moreover, the device incorporates a first one-way valve 26, positioned in the channel that runs through the annular interface 25 and connects the extendable tubular body 24 with the face mask 1. The inlet end of the first one-way valve 26 communicates with the face mask 1, while the outlet end communicates with the interior of the extendable tubular body 24. When the extendable tubular body 24 is compressed, the first one-way valve 26 prevents air inside the extendable tubular body 24 from flowing back into the face mask 1. When extended, it allows air from the face mask 1 to flow into the extendable tubular body 24. The device further includes a second one-way valve 27 located on the negative pressure generating device 2. The outlet end of this valve communicates with the external environment, while the inlet end communicates with the extendable tubular body 24. When the extendable tubular body 24 is compressed, the second one-way valve 27 allows the internal air to escape to the outside. When the extendable tubular body 24 is extended, the second one-way valve 27 closes to prevent air from flowing out and external air from flowing into the second one-way valve 27, thus maintaining a negative pressure environment within the extendable tubular body 24.

In other embodiments, the handle can also be designed as a pull ring or similar form. This design simplifies a design of the grip portion 21 structure found in the first embodiment. For example, in some embodiments since the top of the extendable tubular body 24 is a flat surface, it facilitates neat and orderly stacking of the removal devices during transport, reducing the space they occupy. This allows for more devices to be transported in the same amount of space and makes them easier to carry. Additionally, this simplified design can also streamline the manufacturing process and reduce production costs.

Embodiment 6

Figure 11:
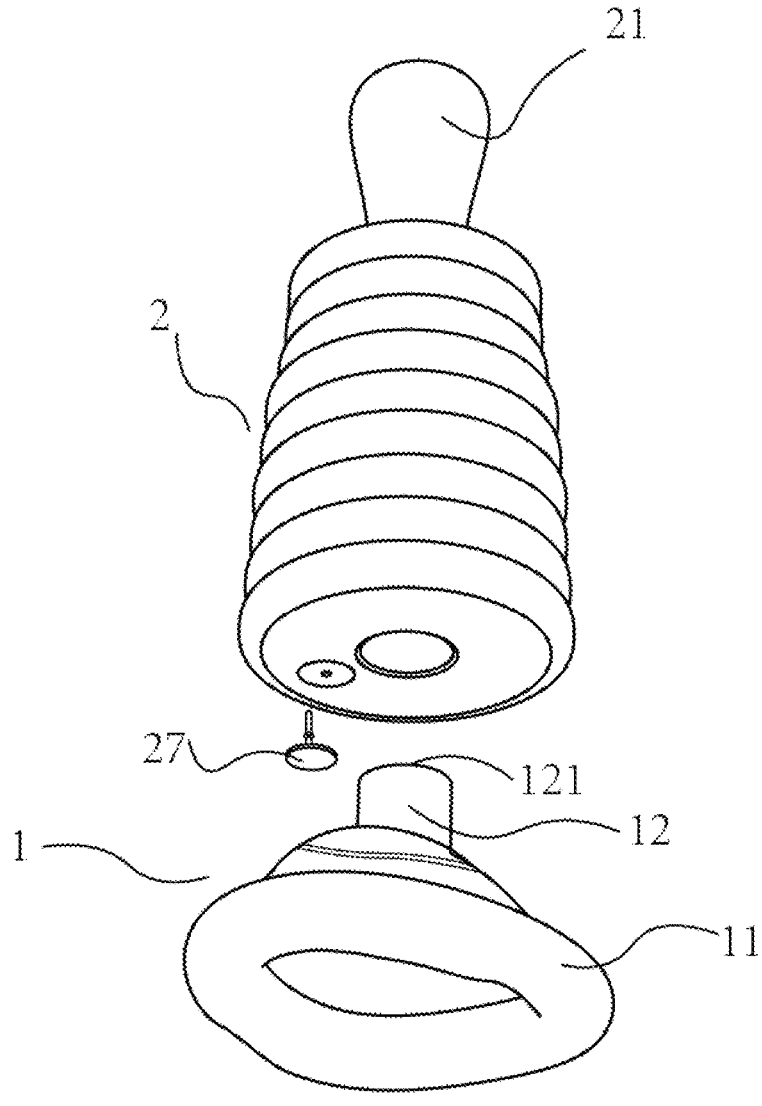
FIG. 11 is a three-dimensional combined schematic diagram of a respiratory obstruction removal device where a second one-way valve is placed on the annular interface, in an embodiment.

This embodiment provides a respiratory obstruction removal device that is easy to carry and transport, as shown in FIG. 11, which illustrates a three-dimensional combined schematic diagram of the respiratory obstruction removal device. The difference between this disclosure and the first embodiment is that the grip portion 21 is non-detachably connected to the extendable tubular body 24.

In this embodiment, the respiratory obstruction removal device includes a grip portion 21 and an extendable tubular body 24, which are non-detachably connected. The extendable tubular body 24 is made of an elastic material and features a variable volume cavity with a hollow structure. One end of the extendable tubular body 24 is connected to the bottom of the grip portion 21. The respiratory obstruction removal device also consists of an annular interface 25 placed at the other end of the extendable tubular body 24 that is far away from the grip portion 21. The annular interface 25 has a face mask interface for connecting to the face mask 1, which includes an upper part 12 that fits with the annular interface 25, a lower part 11, a flexible annular cushion to fit the face of a patient, and a connecting body 13 connecting the upper and lower parts.

The respiratory obstruction removal device also includes a first one-way valve 26, positioned within a channel that runs through the annular interface 25 and connects the extendable tubular body 24 with the face mask 1. The inlet end of the first one-way valve 26 communicates with the face mask 1, and the outlet end communicates with the interior of the extendable tubular body 24. When the extendable tubular body 24 is compressed, the first one-way valve 26 prevents air inside the extendable tubular body 24 from flowing into the face mask 1. When the extendable tubular body 24 is extended, the first one-way valve 26 allows air from inside the face mask 1 to flow into the extendable tubular body 24.

Additionally, the respiratory obstruction removal device further consists of a second one-way valve 27 placed on the grip portion 21. The outlet end of second one-way valve 27 communicates with the external environment, and the inlet end communicates with the extendable tubular body 24. When the extendable tubular body 24 is compressed, the second one-way valve 27 allows air from the extendable tubular body 24 to flow out. When the extendable tubular body 24 is extended, the second one-way valve 27 closes to prevent air from flowing out of the extendable tubular body 24 as well as preventing external air from flowing into it, maintaining a negative pressure environment within the extendable tubular body 24.

Furthermore, it is possible to combine the technical features of the above embodiments as needed to create a respiratory obstruction removal device that includes all or some of these technical features.

Implementing this disclosure offers at least the following beneficial effects:

1. The device of this disclosure is designed to be detachable from its components, disassemblable, which distinguishes it from most of the disposable products currently on the market. This design is environmentally friendly and easier to maintain on a daily basis. In traditional products, if the device is not stored in a completely sealed manner, dust and insects may infiltrate the internal components. The inability to disassemble these traditional designs means that it's difficult to effectively clean such impurities. This could lead to contaminants hidden within the device entering the human body during use or blocking the airflow channels, thereby affecting its performance. Additionally, users often try out the product after purchasing to confirm its efficacy, but if the device can't be cleaned, this could raise hygiene concerns. Moreover, once a disposable product is used for respiratory obstruction removal, its non-disassemblable design means the entire product must be discarded, posing an environmental burden. Therefore, the present design allows for the product to be disassembled, making it convenient for daily cleaning and maintenance. After use, it can also be cleaned and disinfected for reuse, thereby extending the product's lifespan and cost-effectiveness while minimizing its environmental impact. Additionally, reducing the disposal rate of plastic is equivalent to reducing carbon emissions. To some extent, the use of this product accelerates the Earth's progress towards carbon neutrality. It features an eco-friendly design. At the same time, the detachable design of our removal device also has advantages over existing products in terms of disassembly and recycling. Thus, this product is more conducive to recycling, increasing the ease and possibility of circular reuse, and further aligning with the goal of carbon neutrality for the planet. This makes it more recyclable, increasing the ease and likelihood of recycling and further aligning with the global push for carbon neutrality.

2. The respiratory obstruction removal device of this disclosure is optimized with a detachable design, reducing the product's overall size. As a result, more units can be loaded into the same transport space, effectively reducing the number of required transportation vehicles. This design greatly enhances transport efficiency and cost-effectiveness. Not only does it lower logistics costs, but by reducing the number of vehicles needed, it also contributes positively to environmental protection by lowering exhaust emissions. Based on data up to the year 2021, carbon dioxide emissions from road traffic account for approximately 16%-18% of global carbon dioxide emissions. This indicates that road traffic is a significant source of global carbon dioxide emissions. Our product aims to reduce these emissions by decreasing the volume of goods, thereby reducing the number of transport vehicles needed. This, in turn, lowers the consumption and emission of carbon dioxide from automobile exhaust. Our disclosure continues the original intent of moving towards global carbon neutrality by reducing the carbon footprint of vehicles.

3. The reduction in product size offers greater portability for the user. Users can conveniently place the product in a personal bag or the storage compartment of a car's front seat. This design substantially increases the frequency with which users carry the device with them. In the event of a choking emergency, the user can immediately use the device to clear the respiratory obstruction, allowing for quicker and more effective emergency response.

The above descriptions of the disclosure's embodiments are illustrated with reference to the accompanying drawings, but the disclosure is not limited to these specific embodiments. The described embodiments are merely illustrative and not restrictive. Those skilled in the art can make various modifications and variations under the guidance of this disclosure, without departing from the scope and spirit protected by the claims of this disclosure. All such modifications and variations are within the scope of the disclosure's protection.

The invention claimed is:

1. A respiratory obstruction removal device, consisting of:
a negative pressure generating device, and
a flexible annular cushion;
wherein the negative pressure generating device comprises:
an extendable tubular body made of elastic material, comprising a top, bottom, and a variable-volume cavity with a hollow structure in a central portion of the extendable tubular body; and
an annular interface located at the bottom of the extendable tubular body;
the respiratory obstruction removal device further comprising:
a first one-way valve provided within a channel that runs through the annular interface, the flexible annular cushion, and the extendable tubular body, wherein the channel extends between the extendable tubular body and the flexible annular cushion, and wherein an outlet end of the first one-way valve is in fluid communication with an interior of the extendable tubular body, and an inlet end of the first one-way valve is in fluid communication with the flexible annular cushion;
a second one-way valve provided within the negative pressure generating device, wherein an outlet end of the second one-way valve is in fluid communication with an external environment, and an inlet end of the second one-way valve is in fluid communication with the interior of the extendable tubular body,
wherein, when the extendable tubular body is compressed, the first one-way valve is closed to prevent gas from flowing from the extendable tubular body into the flexible annular cushion, and the second one-way valve is configured to allow air to flow from the extendable tubular body to the external environment;
wherein, when the extendable tubular body expands, the first one-way valve is open to allow gas to flow from the flexible annular cushion into the extendable tubular body, and the second one-way valve is closed to prevent gas from flowing out of the extendable tubular body;
wherein the flexible annular cushion is connected via a connecting body along an inner wall of the annular interface, and
wherein the negative pressure generating device comprises a grip portion configured to be handheld and detachable from the extendible tubular body.

2. The respiratory obstruction removal device according to claim 1, wherein the second one-way valve is provided at an interface where the extendable tubular body connects to the grip portion.

3. The respiratory obstruction removal device according to claim 1, wherein the channel is a pathway through which gas flows from the flexible annular cushion into the extendable tubular body when the extendable tubular body, the annular interface, and the flexible annular cushion are connected.

4. The respiratory obstruction removal device according to claim 1, wherein the grip portion has an elastic coefficient greater than that of the extendable tubular body.

5. A respiratory obstruction removal device, consisting of:
a negative pressure generating device, and
a flexible annular cushion;
wherein the negative pressure generating device comprises:
an extendable tubular body made of elastic material, comprising a top, bottom, and a variable-volume cavity with a hollow structure in a central portion of the extendable tubular body;
an annular interface located at the bottom of the extendable tubular body;
the respiratory obstruction removal device further comprising:
a first one-way valve provided within a channel that runs through the annular interface, the flexible annular cushion, and the extendable tubular body, wherein an outlet end of the first one-way valve is in fluid communication with an interior of the extendable tubular body, and an inlet end of the first one-way valve is in fluid communication with the flexible annular cushion;
a second one-way valve provided within the negative pressure generating device, wherein an outlet end of the second one-way valve is in fluid communication with an external environment, and an inlet end of the second one-way valve is in fluid communication with the interior of the extendable tubular body, and
wherein, when the extendable tubular body is compressed, the first one-way valve is closed to prevent gas from flowing from the extendable tubular body into the flexible annular cushion, and the second one-way valve is configured to allow air to flow from the extendable tubular body to the external environment;
wherein, when the extendable tubular body expands, the first one-way valve opens to allow gas to flow from the flexible annular cushion into the extendable tubular body, and the second one-way valve closes to prevent gas from flowing out of the extendable tubular body, with the first one-way valve and second one-way valve being arranged in opposite flow directions;

wherein the flexible annular cushion is connected via a connecting body along an inner wall of the annular interface, and wherein the negative pressure generating device comprises a grip portion configured to be handheld and detachable from the extendible tubular body.

6. The respiratory obstruction removal device according to claim 5, wherein the second one-way valve is provided on either a bottom of the annular interface or the extendable tubular body.

7. The respiratory obstruction removal device according to claim 5, wherein the flexible annular cushion is connected to a mask and the mask and the annular interface are connected through their frictional force.

8. A respiratory obstruction removal device, consisting of:

a negative pressure generating device, and a flexible annular cushion;

wherein the negative pressure generating device comprises:

an extendable tubular body made of elastic material, comprising a top, bottom, and a variable-volume cavity with a hollow structure in a central portion of the extendable tubular body;

an annular interface located at the bottom of the extendable tubular body;

the respiratory obstruction removal device further comprising:

a first one-way valve provided within a channel that runs through the annular interface, the flexible annular cushion, and the extendable tubular body, wherein the channel extends between the extendable tubular body and the flexible annular cushion, wherein an outlet end of the first one-way valve is in fluid communication with an interior of the extendable tubular body, and an inlet end of the first one-way valve is in fluid communication with the flexible annular cushion;

a second one-way valve provided within the negative pressure generating device, wherein an outlet end of the second one-way valve is in fluid communication with an external environment, and an inlet end of the second one-way valve is in fluid communication with the interior of the extendable tubular body, wherein, when the extendable tubular body is compressed, the second one-way valve is configured to allow air to flow from the extendable tubular body to the external environment;

wherein, when the extendable tubular body expands, the second one-way valve closes to prevent air from escaping the extendable tubular body and to block external air from entering, thereby maintaining a negative pressure environment within the extendable tubular body;

wherein the flexible annular cushion is connected via a connecting body along an inner wall of the annular interface, and wherein the negative pressure generating device comprises a grip portion configured to be handheld and detachable from the extendible tubular body.

9. The respiratory obstruction removal device according to claim 8, wherein the top of the negative pressure generating device comprises the grip portion with a threaded combination or a non-hollow grip portion.

10. The respiratory obstruction removal device according to claim 8, wherein the extendable tubular body has a cross-section selected from the group consisting of circular, triangular, polygonal and elliptical shapes.

11. The respiratory obstruction removal device according to claim 8, wherein the grip portion has an anti-slip structure on its outer surface.

12. The respiratory obstruction removal device according to claim 8, wherein, when the extendable tubular body is compressed, the first one-way valve is configured to close to prevent gas in the extendable tubular body from flowing into the flexible annular cushion.

13. A respiratory obstruction removal device, consisting of:

a negative pressure generating device, and a flexible annular cushion;

wherein the negative pressure generating device comprises:

an extendable tubular body made of elastic material, including a top, a bottom, and a variable-volume cavity with a hollow structure at a middle portion of the extendable tubular body;

an annular interface located at the bottom of the extendable tubular body;

the respiratory obstruction removal device further comprising:

a first one-way valve provided within a channel that runs through the annular interface, the flexible annular cushion, and the extendable tubular body, wherein the channel extends between the extendable tubular body and the flexible annular cushion, and wherein an outlet end of the first one-way valve is in fluid communication with an interior of the extendable tubular body, and an inlet end of the first one-way valve is in fluid communication with the flexible annular cushion;

a second one-way valve provided within the negative pressure generating device, wherein an outlet end of the second one-way valve is in fluid communication with an external environment, and an inlet end of the second one-way valve is in fluid communication with the interior of the extendable tubular body, wherein, when the extendable tubular body is compressed, the first one-way valve closes to prevent air from flowing from the extendable tubular body to the external environment;

wherein, when the extendable tubular body expands, the first one-way valve opens to allow air to enter the extendable tubular body;

wherein the flexible annular cushion is connected via a connecting body along an inner wall of the annular interface, and wherein the negative pressure generating device comprises a grip portion configured to be handheld and detachable from the extendible tubular body.

14. The respiratory obstruction removal device according to claim 13, wherein the annular interface and the extendable tubular body have connection points with uniform sizes.

15. The respiratory obstruction removal device according to claim 13, wherein the flexible annular cushion is configured to surround a patient's mouth and to fit against the patient's face.

16. The respiratory obstruction removal device according to claim 13, wherein the extendable tubular body comprises a material and structure such that an elastic coefficient of the extendable tubular body in an axial direction is smaller than an elastic coefficient of the extendable tubular body in other directions, thereby allowing for greater deformation along the axial direction.

17. The respiratory obstruction removal device according to claim 13, wherein when the extendable tubular body expands, the second one-way valve is closed to prevent gas from exiting the extendable tubular body to the external environment and to prevent external gas from entering the extendable tubular body.

\* \* \* \* \*